(12) United States Patent
Sudo et al.

(10) Patent No.: US 10,752,977 B2
(45) Date of Patent: Aug. 25, 2020

(54) PALLADIUM SEPARATING AGENT, METHOD FOR PRODUCING SAME AND USE OF SAME

(71) Applicant: TOSOH CORPORATION, Shunan-shi, Yamaguchi (JP)

(72) Inventors: Yukinori Sudo, Shunan (JP); Takahiro Masuda, Shunan (JP); Setsuo Yoshida, Shunan (JP)

(73) Assignee: TOSOH CORPORATION, Shunan-shi, Yamaguchi (JP)

( * ) Notice: Subject to any disclaimer, the term of this patent is extended or adjusted under 35 U.S.C. 154(b) by 237 days.

(21) Appl. No.: 14/349,870

(22) PCT Filed: Oct. 5, 2012

(86) PCT No.: PCT/JP2012/076026
§ 371 (c)(1),
(2) Date: Apr. 4, 2014

(87) PCT Pub. No.: WO2013/051715
PCT Pub. Date: Apr. 11, 2013

(65) Prior Publication Data
US 2014/0248198 A1 Sep. 4, 2014

(30) Foreign Application Priority Data
Oct. 7, 2011 (JP) ................................. 2011-223423

(51) Int. Cl.
*B01J 20/289* (2006.01)
*C07C 323/60* (2006.01)
(Continued)

(52) U.S. Cl.
CPC .............. *C22B 11/04* (2013.01); *B01D 15/08* (2013.01); *B01J 20/289* (2013.01);
(Continued)

(58) Field of Classification Search
CPC .. B01J 20/3251; B01J 20/289; B01J 20/3204; B01J 20/3219; B01J 20/3425;
(Continued)

(56) References Cited

U.S. PATENT DOCUMENTS 2,910,373 A   10/1959 Chenicek et al.
5,618,433 A *  4/1997 Tarbet ................. B01J 45/00
                                          210/321.6

(Continued)

FOREIGN PATENT DOCUMENTS

EP       0947467     * 10/1999  .............. B01J 20/32
JP       9-279264 A    10/1997
(Continued)

OTHER PUBLICATIONS

Machine translation of WO2011021696A1 Date:Feb. 2011.*

(Continued)

*Primary Examiner* — Bobby Ramdhanie
*Assistant Examiner* — Donovan Bui-Huynh
(74) *Attorney, Agent, or Firm* — Sughrue Mion, PLLC

(57) ABSTRACT

To provide a palladium separating agent capable of separating palladium ions from a solution containing palladium ions of a low concentration to a high concentration in a short time with a high selectivity, and a method for separating palladium.

A palladium separating agent having a functional group represented by the formula (1) bonded to a carrier:

$$-Z-(CH_2)_n-S-R \qquad (1)$$

wherein R is a $C_{1-18}$ chain hydrocarbon group, a $C_{3-10}$ alicyclic hydrocarbon group, a $C_{6-14}$ aromatic hydrocarbon group, a carboxymethyl group or a carboxyethyl group, n is an integer of from 1 to 4, and Z is an amide bond.

10 Claims, 1 Drawing Sheet

(51) Int. Cl.
| | | |
|---|---|---|
| B01D 15/08 | (2006.01) | |
| B01J 20/32 | (2006.01) | |
| B01J 20/34 | (2006.01) | |
| C02F 101/20 | (2006.01) | |
| C02F 1/68 | (2006.01) | |
| C02F 1/00 | (2006.01) | |
| C02F 1/42 | (2006.01) | |
| C22B 3/00 | (2006.01) | |
| C22B 3/42 | (2006.01) | |
| C02F 1/28 | (2006.01) | |
| C02F 1/70 | (2006.01) | |
| C02F 1/66 | (2006.01) | |
| C02F 1/461 | (2006.01) | |

(52) U.S. Cl.
CPC ....... *B01J 20/3204* (2013.01); *B01J 20/3219* (2013.01); *B01J 20/3251* (2013.01); *B01J 20/345* (2013.01); *B01J 20/3425* (2013.01); *C02F 1/285* (2013.01); *C07C 323/60* (2013.01); *C22B 3/42* (2013.01); *C02F 1/004* (2013.01); *C02F 1/288* (2013.01); *C02F 1/42* (2013.01); *C02F 1/461* (2013.01); *C02F 1/66* (2013.01); *C02F 1/683* (2013.01); *C02F 1/70* (2013.01); *C02F 2101/20* (2013.01); *C02F 2303/16* (2013.01); *C07B 2200/11* (2013.01); *Y02P 10/234* (2015.11)

(58) Field of Classification Search
CPC ........ B01J 20/345; B01D 15/08; C02F 1/285; C02F 1/004; C02F 1/288; C02F 1/42; C02F 1/461; C02F 1/66; C02F 1/683; C02F 1/70; C02F 2101/20; C02F 2303/16; C07C 323/60; C22B 11/04; C22B 3/42; C07B 2200/11
See application file for complete search history.

(56) References Cited

U.S. PATENT DOCUMENTS

| | | | |
|---|---|---|---|
| 2006/0194145 A1* | 8/2006 | Irvine | B82Y 30/00 430/270.1 |
| 2007/0072199 A1* | 3/2007 | Levicky | B01J 20/289 435/6.12 |
| 2007/0172404 A1 | 7/2007 | Narita et al. | |
| 2009/0178513 A1 | 7/2009 | Narita et al. | |
| 2011/0076246 A1 | 3/2011 | Haley et al. | |
| 2011/0143101 A1* | 6/2011 | Sandhu | B82Y 30/00 428/195.1 |

FOREIGN PATENT DOCUMENTS

| | | | | |
|---|---|---|---|---|
| JP | 2010-59533 A | | 3/2010 | |
| JP | 2011041916 | * | 3/2011 | ............. B01J 20/22 |
| WO | 9725139 A1 | | 7/1997 | |
| WO | 2004018071 A2 | | 3/2004 | |
| WO | 2004113872 A2 | | 12/2004 | |
| WO | 2005/083131 A1 | | 9/2005 | |
| WO | 2011021696 A1 | | 2/2011 | |
| WO | WO2011021696 A1 | * | 2/2011 | ............. B01J 38/00 |
| WO | WO2012129380 | * | 12/2012 | ............. C07B 45/00 |

OTHER PUBLICATIONS

Machine translation of JP2011041916 Date: Mar. 2011.*
Communication dated Jul. 21, 2015 from the European Patent Office issued in corresponding application No. 12838925.1.
Ijuin, Wataru, et al, "Thiapentanediamide Kagaku Ketsugogata Silica o Mochiiru Platina-zoku Kinzoku no Kaishu", The Japan Society for Analytical Chemistry Nenkai Koen Yoshishu, vol. 59th, The Japan Society for Analytical Chemistry, Sep. 1, 2010 (Sep. 1, 2010), p. 98.

* cited by examiner

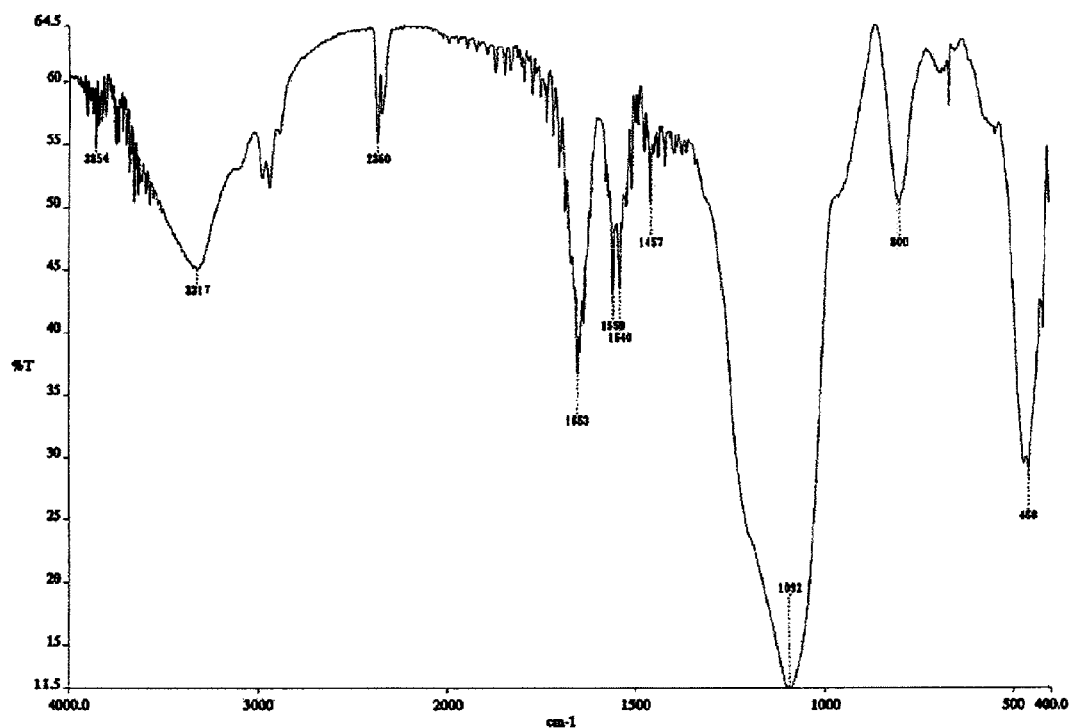

PALLADIUM SEPARATING AGENT, METHOD FOR PRODUCING SAME AND USE OF SAME

CROSS REFERENCE TO RELATED APPLICATIONS

This application is a National Stage of International Application No. PCT/JP2012/076026, filed on Oct. 5, 2012, which claims priority from Japanese Patent Application No. 2011-223423, filed on Oct. 7, 2011, the contents of all of which are incorporated herein by reference in their entirety.

TECHNICAL FIELD

The present invention relates to a palladium separating agent which selectively adsorbs palladium ions from a solution containing a plural types of metal ions and is thereby capable of separating and recovering palladium, its production method and its use.

BACKGROUND ART

For industrial catalysts, automobile exhaust gas purifying catalysts and many electric appliances, precious metals such as palladium, platinum and rhodium have been used. Since such precious metals are expensive and useful as resources, they have been recovered after use and reused, that is, recycled. In recent years, demands for the resources conservation are increasing, and importance of recycle of precious metals is more increasing.

To recover a precious metal, many methods such as a sedimentation separation method, an ion exchange method, an electrodeposition method, a solvent extraction method and an adsorption method have been developed, and among them, a solvent extraction method has been widely employed in view of the economical efficiency and operation property.

A solvent extraction method comprises an extracting step of subjecting an aqueous phase in which palladium ions are dissolved and an organic phase in which a palladium ion extracting agent is dissolved to liquid-liquid contact to extract the palladium ions into the organic phase side, and a back extraction step of back-extracting the palladium ions into the aqueous phase side by bringing the palladium ions which had been extracted to the organic phase side into contact with an aqueous phase in which a back-extracting agent is dissolved (for example, Patent Documents 1 and 2).

However, the solvent extraction method has problems in view of the safety and the environmental burden, since a large quantity of an organic solvent is used. Further, a disulfide compound such as dioctyl sulfide or dihexyl sulfide, commonly used as the extracting agent for the extracting method is likely to be oxidized, and accordingly its repeated use is problematic.

To solve such problems, a palladium separating agent has been proposed, which can be reused by improving the structure of the dialkyl sulfide by introducing an amide group to the vicinity of S thereby to prevent oxidation of the disulfide compound (for example, Patent Document 3).

However, even this palladium separating agent provides an insufficient selectivity of separation of palladium from a solution containing palladium ions at a high concentration, and it has been desired to develop a separating agent capable of separating palladium from a palladium ion solution of a low concentration to a high concentration in a short time with a high selectivity, and a method for separating palladium.

PRIOR ART DOCUMENTS

Patent Documents

Patent Document 1: JP-A-9-279264
Patent Document 2: JP-A-2010-59533
Patent Document 3: WO2005083131

DISCLOSURE OF INVENTION

Technical Problem

Under these circumstances, the object of the present invention is to provide a palladium separating agent capable of separating palladium from a palladium solution of a low concentration to a high concentration in a short time with a high selectivity, and a method for separating palladium.

Solution to Problem

The present inventors have conducted extensive studies to achieve the above object and as a result, they have found that a novel palladium separating agent of the present invention, particularly a palladium separating agent having a high S/N (element ratio) of the S element to the N element in the palladium separating agent, is capable of separating palladium from a high concentration palladium solution in a short time with a high selectivity, as compared with a conventional palladium separating agent, and accomplished the present invention. That is, the present invention provides the following.

[1] A palladium separating agent having a functional group represented by the formula (1) bonded to a carrier:

wherein R is a $C_{1-18}$ chain hydrocarbon group, a $C_{3-10}$ alicyclic hydrocarbon group, a $C_{6-14}$ aromatic hydrocarbon group, a carboxymethyl group or a carboxyethyl group, n is an integer of from 1 to 4, and Z is an amide bond.

[2] The palladium separating agent according to the above [1], wherein the functional group represented by the formula (1) is a functional group represented by the formula (2):

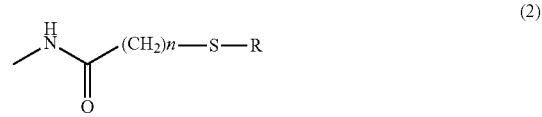

wherein R is a $C_{1-18}$ chain hydrocarbon group, a $C_{3-10}$ alicyclic hydrocarbon group, a $C_{6-14}$ aromatic hydrocarbon group, a carboxymethyl group or a carboxyethyl group, and n is an integer of from 1 to 4.

[3] The palladium separating agent according the above [1] or [2], wherein the functional group represented by the formula (1) or (2) is bonded to the carrier by means of a methylene group, an ethylene group, a $C_{3-8}$ linear, branched or cyclic alkylene group or a $C_{6-14}$ arylene group.

[4] The palladium separating agent according to the above [3], wherein the functional group represented by the formula (1) or (2) is bonded to the carrier by means of a n-propylene group.

[5] The palladium separating agent according to any one of the above [1] to [4], wherein R in the formula (1) or (2) is a methyl group, an ethyl group, a propyl group, a butyl group, an isopropyl group, a phenyl group or a benzyl group.
[6] The palladium separating agent according to any one of the above [1] to [5], wherein in the formula (1) or (2), n is an integer of 1.
[7] The palladium separating agent according to any one of the above [1] to [6], wherein the carrier is an inorganic carrier.
[8] The palladium separating agent according to the above [7], wherein the inorganic carrier is a silica gel.
[9] The palladium separating agent according to any one of the above [1] to [8], wherein the element ratio (S/N) of the S element to the N element contained in the palladium separating agent is from 0.94 to 1.00, and the average pore size of the carrier is at least 2 nm.
[10] A method for producing a palladium separating agent, which comprises reacting a sulfide-containing carboxylic acid compound represented by the formula (3) with a carrier having an amino group to obtain a palladium separating agent having a functional group represented by the formula (1) bonded to the carrier:

$$-Z-(CH_2)n\text{-}S-R \tag{1}$$

wherein R is a $C_{1\text{-}18}$ chain hydrocarbon group, a $C_{3\text{-}10}$ alicyclic hydrocarbon group, a $C_{6\text{-}14}$ aromatic hydrocarbon group, a carboxymethyl group or a carboxyethyl group, n is an integer of from 1 to 4, and Z is an amide bond;

$$H_2O-(CH_2)_n-S-R \tag{3}$$

wherein R is a $C_{1\text{-}18}$ chain hydrocarbon group, a $C_{3\text{-}10}$ alicyclic hydrocarbon group, a $C_{6\text{-}14}$ aromatic hydrocarbon group, a carboxymethyl group or a carboxyethyl group, and n is an integer of from 1 to 4.
[11] The method for producing a palladium separating agent according to the above [10], wherein the carrier having an amino group is one obtained by reacting a silane coupling agent having an amino group represented by the formula (4) with a carrier:

$$(X)_{\overline{3}}Si-Y \tag{4}$$

wherein each of X's which are independent of one another, is a methyl group, an ethyl group, a methoxy group or an ethoxy group, provided that at least one of them is a methoxy group or an ethoxy group, and Y is a $C_{1\text{-}12}$ aminoalkyl group having from 1 to 2 nitrogen atoms.
[12] A method for adsorbing palladium ions, which comprises bringing the palladium separating agent as defined in any one of the above [1] to [9] into contact with a solution containing palladium ions.
[13] A method for desorbing palladium ions, which comprises bringing the palladium separating agent in which palladium ions are adsorbed, obtained by the method for adsorbing palladium ions as defined in the above [12], into contact with a desorbing agent.
[14] The method for desorbing palladium ions according to the above [13], wherein the desorbing agent is ammonia, thiourea or methionine.
[15] A chromatography column, which is packed with the palladium separating agent as defined in any one of the above [1] to [9].

Advantageous Effects of Invention

According to the present invention, it is possible to provide a palladium separating agent having a high palladium ion selectivity and having a high palladium ion adsorption amount even under high hydrochloric acid concentration conditions.

Further, the palladium separating agent of the present invention is capable of adsorbing and separating palladium ions highly selectively from a solution in which platinum ions coexist at a high concentration, can be repeatedly used, and does not require an organic solvent. Thus, separation and recovery of palladium ions can be carried out economically efficiently without imposing an environmental burden.

Still further, by the present invention, palladium can be separated from a high concentration palladium solution in a short time with a high selectivity, and palladium ions can be separated and recovered efficiently as compared with a conventional palladium separating agent.

BRIEF DESCRIPTION OF DRAWING

FIG. 1 is a drawing illustrating results of infrared spectroscopic analysis of a palladium separating agent A in Example 1.

DESCRIPTION OF EMBODIMENTS

Now, the present invention will be described in detail below.

The palladium separating agent of the present invention has a functional group represented by the formula (1) bonded to a carrier:

$$-Z-(CH_2)n\text{-}S-R \tag{1}$$

wherein R is a $C_{1\text{-}18}$ chain hydrocarbon group, a $C_{3\text{-}10}$ alicyclic hydrocarbon group, a $C_{6\text{-}14}$ aromatic hydrocarbon group, a carboxymethyl group or a carboxyethyl group, n is an integer of from 1 to 4, and Z is an amide bond represented by —CONH—.

Further, the palladium separating agent of the present invention is a palladium separating agent wherein the functional group represented by the formula (1) is a functional group represented by the formula (2):

$$\underset{\underset{H}{N}}{\overset{}{\diagdown}}\underset{\underset{O}{\|}}{\overset{}{C}}(CH_2)n-S-R \tag{2}$$

wherein R and n are the same as those in the formula (1).

Further, in the formula (1) or (2), n is preferably an integer of 1.

The functional group represented by the formula (1) or (2) is preferably bonded to the carrier by means of a methylene group, an ethylene group, a $C_{3\text{-}8}$ linear, branched or cyclic alkylene group or a $C_{6\text{-}14}$ arylene group.

The $C_{3\text{-}8}$ linear or branched alkylene group is not particularly limited and may, for example, be a propylene group, a butylene group, a pentylene group, a hexylene group, a heptylene group or an octylene group. They may be linear or branched. The position of bonding of the amide group is not particularly limited so long as the amide group is on the carbon atom of the alkylene group.

The $C_{3\text{-}8}$ cyclic alkylene group may, for example, be a cyclopropylene group, a cyclobutylene group, a cyclopentylene group, a cyclohexylene group, a cycloheptylene group, a cyclooctylene group, a cyclohexenylene group, a cyclohexadienylene group, a cyclooctenylene group or a cyclooctadienylene group. In the cyclic alkylene group also, the position of bonding of the amide group is not particularly limited so long as the amide group is on the carbon atom of the cycloalkylene group.

Further, the $C_{6-14}$ arylene group may, for example be a phenylene group, a naphthylene group, an anthrylene group, a tolylene group, a xylylene group, a cumenylene group, a benzylene group, a phenetylene group, a styrylene group, a cinnamylene group, a biphenylene group or a phenanthrylene group. In the arylene group also, the position of bonding of the amide group is not particularly limited so long as the amide group is on the carbon atom of the arylene group.

Among them, a n-propylene group is particularly preferred.

In the functional group represented by each of the formulae (1) and (2), R is a $C_{1-18}$ chain hydrocarbon group, a $C_{3-10}$ alicyclic hydrocarbon group, a $C_{6-14}$ aromatic hydrocarbon group, a carboxymethyl group or a carboxyethyl group.

The $C_{1-18}$ chain hydrocarbon group is not particularly limited and may, for example, be a methyl group, an ethyl group, a propyl group, a butyl group, a pentyl group, a hexyl group, a heptyl group, an octyl group, a nonyl group, a decyl group, an undecyl group, a dodecyl group, a tridecyl group, a tetradecyl group, a pentadecyl group, a hexadecyl group (cetyl group), a heptadecyl group, an octadecyl group (stearyl group), an oleyl group, an elaidyl group, an isopropyl group, an isobutyl group, a sec-butyl group, a tert-butyl group, an isopentyl group, a neopentyl group, a tert-pentyl group, a 2-ethylhexyl group, a vinyl group, an allyl group, a 1-propenyl group, an isopropenyl group, a 1-butenyl group, a 2-butenyl group, a 2-methylallyl group, a 1-heptynyl group, a 1-hexenyl group, a 1-heptenyl group, a 1-octenyl group or a 2-methyl-1-propenyl group.

The $C_{3-10}$ alicyclic hydrocarbon group is not particularly limited and may, for example, be a cyclopropyl group, a cyclobutyl group, a cyclopentyl group, a cyclohexyl group, a cycloheptyl group, a cyclooctyl group, a cyclononyl group, a cyclodecyl group, a cyclohexenyl group, a cyclohexadienyl group, a cyclooctenyl group or a cyclooctadienyl group.

The $C_{6-14}$ aromatic hydrocarbon group is not particularly limited and may, for example, be a phenyl group, a naphthyl group, an anthryl group, a tolyl group, a xylyl group, a cumenyl group, a benzyl group, a phenethyl group, a styryl group, a cinnamyl group, a biphenyl group or a phenanthryl group.

R is preferably a methyl group, an ethyl group, a propyl group, a butyl group, an isopropyl group, a phenyl group or a benzyl group, more preferably an ethyl group, a propyl group, an isopropyl group, a phenyl group or a benzyl group, particularly preferably an ethyl group or a propyl group.

In the functional group represented by each of the formulae (1) and (2), n is an integer of from 1 to 4, preferably 1.

In the functional group represented by the formula (1), Z is an amide bond. Here, the amide bond is a bond represented by —CO—NH—, and the direction of the bond is not limited, but is preferably the direction represented by the formula (2).

The carrier is not particularly limited so long as it is insoluble in a solvent. The carrier which can be used is not particularly limited and may, for example, be an inorganic carrier such as silica gel, alumina, titania, magnesia, zirconia, iron oxide, copper oxide, glass, silica sand, talc, mica, clay or wollastonite; a polystyrene polymer such as a styrene polymer or a styrene/divinylbenzene crosslinked product; a polyolefin such as polyethylene, polypropylene or polyvinyl chloride; an acrylic polymer such as polymethyl methacrylate or polyethyl methacrylate; or an organic carrier such as polylysine particles, polyvinylamine particles, polymethylglutamic acid or polyvinyl alcohol. Among these carriers, preferred is an inorganic carrier in view of the chemical resistance and the cost, particularly preferred is a silica gel in view of high versatility.

The form of the carrier may be any form commonly employed as a separation substrate, such as spheres (for example, spherical particles), particles, fibers, granules, monolith columns, hollow fibers or a membrane (for example, flat membrane), and is not particularly limited. Among them, the form of spheres, a membrane, particles, granules or fibers is preferred. The carrier in the form of spheres, particles or granules is particularly preferred, since the volume of use can freely be set when used for a column method or a batch method.

The particle size of the carrier in the form of spheres, particles or granules is not particularly limited, and for example, one having an average particle size within a range of from 1 μm to 10 mm may be used. Further, the average particle size is preferably within a range of from 2 μm to 1 mm in view of the operation property and the adsorption capacity.

The element ratio (S/N) of the S element to the N element contained in the palladium separating agent may be calculated, for example, by elemental analysis. The element ratio (S/N) is not particularly limited, and is preferably from 0.94 to 1.00. If it is lower than 0.94, the palladium ion selectivity may be low in some cases.

The average pore size of the carrier may be calculated, for example, by a BET method. The average pore size is not particularly limited, and is preferably at least 2 nm. If it is smaller than 2 nm, the palladium ion adsorption amount may be small in some cases.

A method for producing the palladium separating agent having the functional group of the above formula (1) bonded to the carrier by means of an amide bond or the palladium separating agent having the functional group represented by the formula (2) bonded to the carrier is not particularly limited, and for example, the following method may be mentioned. That is, the palladium separating agent can be produced by reacting the after-mentioned carrier having an amino group (hereinafter referred to as "aminated carrier") with a sulfide-containing carboxylic acid compound represented by the following formula (3) (hereinafter referred to as "fixation reaction"):

$$HO_2C-(CH_2)_n-S-R \qquad (3)$$

wherein R is a $C_{1-18}$ chain hydrocarbon group, a $C_{3-10}$ alicyclic hydrocarbon group, a $C_{6-14}$ aromatic hydrocarbon group, a carboxymethyl group or a carboxyethyl group, and n is an integer of from 1 to 4.

The sulfide-containing carboxylic acid compound represented by the formula (3) may be a sulfide-containing carboxylate such as an ammonium salt or an alkali metal salt, an esterified product such as a methyl carboxylate or an ethyl carboxylate, or an acid anhydride formed by dehydration condensation of two molecules of the sulfide-containing carboxylic acid compound.

The aminated carrier is not particularly limited, and a commercially available product may be used, or one obtained by aminating the above carrier by a known method may be used.

The aminated carrier is not particularly limited, and may, for example, be specifically an aminated inorganic carrier such as aminated silica gel, aminated alumina, aminated zirconia, aminated titania, aminated magnesia or aminated glass, an aminated styrene/divinylbenzene crosslinked product, polyallylamine particles, polylysine particles, polyvinylamine particles, aminated polymethylglutamic acid or aminated polyvinyl alcohol.

The aminated inorganic carrier or the like may be produced, for example, by mixing and reacting the above inorganic carrier and a silane coupling agent having an amino group (hereinafter referred to as "silane coupling reaction"), although not particularly limited.

The silane coupling agent having an amino group is not particularly limited and may, for example, be a silane coupling agent represented by the formula (4):

$$(X)_3\text{-Si}-Y \quad (4)$$

wherein each of X's which are independent of one another, is a methyl group, an ethyl group, a methoxy group or an ethoxy group, provided that at least one of them is a methoxy group or an ethoxy group, and Y is a $C_{1\text{-}12}$ aminoalkyl group having from 1 to 2 nitrogen atoms.

In the formula (4), the $C_{1\text{-}12}$ amino alkyl group having from 1 to 2 nitrogen atoms represented by Y is not particularly limited and may, for example, be a 2-aminoethyl group, a 3-aminopropyl group, a 6-aminohexyl group, a N-2-(aminoethyl)-3-aminopropyl group or a N-6-(aminohexyl)-3-aminopropyl group.

The amount of use of the silane coupling agent having an amino group in the silane coupling reaction is not particularly limited and may, for example, be within a range of from 0.1 to 10 mol per 1 kg of the carrier. It is preferably within a range of from 0.5 to 5 mol in view of the efficiency of introduction of the amino group and the economical efficiency.

The above silane coupling reaction is carried out usually in a solvent. The solvent is not particularly limited so long as it does not inhibit the reaction, and is preferably an aromatic hydrocarbon solvent such as benzene, toluene, xylene or mesitylene. The amount of use of the solvent is not particularly limited and is usually from 2 to 40 parts by weight, preferably from 4 to 15 parts by weight to the silane coupling agent having an amino group.

The reaction temperature in the silane coupling reaction is preferably within a range of from 0 to 200° C., more preferably from 30 to 110° C. Within such a temperature range, the silane coupling reaction will sufficiently proceed.

The reaction time in the silane coupling reaction varies depending upon the concentration of the silane coupling agent having an amino group, the reaction temperature, etc. and is usually within a range of from several minutes to 24 hours.

The aminated carrier obtained by the silane coupling reaction can easily be separate from other components in the reaction liquid by filtration and washing.

The amount of use of the sulfide-containing carboxylic acid compound represented by the formula (3) in the fixation reaction is preferably from 1 to 10 molar times, more preferably from 1.2 to 3 molar times to the nitrogen content of the aminated carrier. When the amount of use of the sulfide-containing carboxylic acid compound is at least 1 molar time to the nitrogen content of the aminated carrier, the fixation reaction will sufficiently proceed, and when it is at most 10 molar times, such is economically preferred.

The fixation reaction is carried out usually in a solvent. The solvent is not particularly limited so long as it does not inhibit the reaction and is preferably an organic solvent such as benzene, toluene, xylene, dichloromethane, chloroform, tetrahydrofuran or N,N-dimethylformamide. The amount of use of the solvent is not particularly limited and is usually from 2 to 40 parts by weight, preferably from 3 to 15 parts by weight to the sulfide-containing carboxylic acid compound represented by the formula (3).

In the fixation reaction, a reaction accelerating agent may be added to the reaction liquid. The reaction accelerating agent is not particularly limited and may, for example, be a dehydration condensation agent such as N,N'-dicyclohexylcarbodiimide, N,N'-diisopropylcarbodiimide, 1-ethyl-3-(3-dimethylaminopropyl)carbodiimide, diphenylphosphoryl azide, benzotriazol-1-yloxy-trisdimethylaminophosphonium chloride or 4-(4,6-dimethoxy-1,3,5-triazin-2-yl)-4-methylmorpholinium chloride, or a boronic acid derivative such as 3,5-bis(trifluoromethyl)phenylboronic acid, 4-trifluoromethylphenylboronic acid, 3,4,5-trifluorophenylboronic acid or 3-nitrophenylboronic acid. As such a dehydration condensation agent or boronic acid derivative, a commercially available reagent may be used as it is.

The amount of use of the dehydration condensation agent is within a range of from 1 to 10 molar times to 1 mol of the sulfide-containing carboxylic acid compound represented by the formula (3), and is preferably within a range of from 1 to 3 molar times in view of the reaction accelerating effect and the economical efficiency. In a case where the dehydration condensation agent is used, for the purpose of improving the reactivity, an additive such as 1-hydroxybenzotriazole, 1-hydroxy-7-azabenzotriazole or N-hydroxysuccinimide may further be added.

The amount of use of such an additive is within a range of from 1 to 10 molar times to 1 mol of the sulfide-containing carboxylic acid compound represented by the formula (3), and is preferably within a range of from 1 to 3 molar times in view of the reaction accelerating effect and the economical efficiency.

Further, the amount of use of the boronic acid derivative is within a range of from 0.0001 to 1 molar time to 1 mol of the sulfide-containing carboxylic acid compound represented by the formula (3), and is preferably within a range of from 0.001 to 0.5 molar time in view of the reaction accelerating effect and the economical efficiency, further preferably within a range of from 0.005 to 0.1 molar time.

The reaction temperature in the fixation reaction is preferably within a range of from 0 to 200° C., more preferably within a range of from 100 to 180° C.

The reaction time in the fixation reaction varies depending upon the concentrations of the sulfide-containing carboxylic acid compound represented by the formula (3) and the reaction accelerating agent, the reaction temperature, etc., and is usually within a range of from several minutes to 24 hours.

The palladium separating agent obtained by the above fixation reaction can easily be separated from other components in the reaction liquid by an operation such as filtration, washing or drying.

The palladium separating agent of the present invention may also be produced by a method other than the above production method.

The production method other than the above method may, for example, be a production method of reacting a sulfide-containing amine compound represented by the formula (5) such as 2-aminoethyl methyl sulfide, 2-aminoethyl ethyl sulfide or 3-aminopropyl methyl sulfide with a carrier having a carboxy group. On that occasion, as the reaction conditions, conventional reaction conditions may be employed, and reaction conditions similar to the above-described reaction conditions are preferably employed.

$$H_2N\text{---}(CH_2)_n\text{---}S\text{---}R \quad (5)$$

wherein R is a $C_{1-18}$ chain hydrocarbon group, a $C_{3-10}$ alicyclic hydrocarbon group, a $C_{6-14}$ aromatic hydrocarbon group, a carboxymethyl group or a carboxyethyl group, and n is an integer of from 1 to 4.

The sulfide-containing amine compound represented by the formula (5) may be used in the form of a salt such as a hydrochloride or a bromate.

As the carrier having a carboxy group, a known carrier having a carboxy group may be used. Otherwise, a carrier having a carboxy group introduced to the surface of a known carrier by a known method may be used. On that occasion, the carboxy group may be esterified to be a carboxymethyl group, a carboxyethyl group or the like.

The carrier having a known carboxy group is not particularly limited and may, for example, be a silica gel having a carboxy group (such as SC carboxy group-modified silica microspheres, manufactured by NIPPN TECHNO CLUSTER, INC) or an ion exchange resin having carboxy groups.

Further, as a production method other than the above, although not particularly limited, for example, a method of chemically binding a sulfide-containing carboxylic acid compound having a substituent represented by the formula (1) or (2) to a carrier by a known method may also be employed. For example, although not particularly limited, a method of reacting a reaction product of the sulfide-containing carboxylic acid compound represented by the formula (3) and the silane coupling agent having an amino group represented by the formula (4) with an inorganic carrier may be mentioned.

Now, methods for adsorbing and desorbing palladium ions of the present invention will be described.

Adsorption of palladium ions by the palladium separating agent of the present invention is carried out by bringing the palladium separating agent into contact with a solution containing palladium ions.

A method for bringing the solution containing palladium ions into contact with the palladium separating agent of the present invention is not particularly limited and may, for example, be a method (fluidized bed) of preparing a slurry by mixing the solution containing palladium ions and the palladium separating agent, and stirring the slurry. Further, a method (fixed bed) of packing the palladium separating agent in a column or the like and passing the solution containing palladium ions through the column or the like may also be mentioned.

In the above method for adsorbing palladium ions, the solution containing palladium ions to be brought into contact with the palladium separating agent of the present invention is not particularly limited and may, for example, be a solution in which an automobile exhaust gas purifying catalyst or jewelry is dissolved, or a solution after acid leaching in a step of wet defining of platinum group metals.

The solution containing palladium ions may contain platinum group metal ions such as platinum ions or rhodium ions or base metal ions such as copper ions, iron ions, nickel ions or zinc ions, in addition to palladium ions. By bringing the solution into contact with the palladium separating agent of the present invention, palladium ions can selectively be adsorbed.

The solution containing palladium ions is not particularly limited and is preferably an aqueous solution in view of the environmental burden.

The pH of the solution containing palladium ion is not particularly limited, and the solution is preferably acidic. The acid to be used to make the solution containing palladium ions acidic is not particularly limited and may, for example, be an inorganic acid such as hydrochloric acid, sulfuric acid or nitric acid. Among them, hydrochloric acid is particularly preferred, which is used as an acid leaching liquid for palladium ions.

The acid concentration in the solution containing palladium ions is not particularly limited and is preferably within a range of from 0.1 to 10 mol/L (liter), more preferably from 0.1 to 5 mol/L. Within such an acid concentration, adsorption of palladium ions can be carried out without impairing the adsorption efficiency of the palladium separating agent.

In the method for adsorbing palladium ions, the amount of use of the palladium separating agent of the present invention is such that the amount of sulfur in the palladium separating agent is preferably from 0.1 to 100 molar times, more preferably from 0.5 to 10 molar times, to 1 mol of the palladium ions in the solution containing palladium ions.

To desorb the palladium ions from the palladium separating agent of the present invention in which the palladium ions are adsorbed, the palladium separating agent in which the palladium ions are adsorbed is brought into contact with a desorbing agent.

A method for bringing the palladium separating agent in which the palladium ions are adsorbed into contact with the desorbing agent is not particularly limited and may, for example, be contact under the same conditions as in the method for adsorbing palladium ions.

The desorbing agent used in the method for desorbing palladium ions is not particularly limited and may, for example, be ammonia, thiourea, methionine or ethylenediamine. Among them, thiourea or methionine is preferred in view of the desorption efficiency and the desorption rate, and ammonia is preferred in view of the economical efficiency. Such a desorbing agent is preferably properly selected depending upon the physical properties of the carrier.

The desorbing agent may be used as a commercially available product as it is when it is a liquid, or may be used as a solution dissolved in an optional solvent. In a case where it is used as a desorbing agent solution, it may be used, for example, as an organic solution, an organic/aqueous mixed solution, an aqueous solution or an acidic aqueous solution, although not particularly limited. Among them, it is preferably used as an aqueous solution or an acidic aqueous solution in view of the environmental burden. Further, in the case of an acidic aqueous solution, an inorganic acid such as hydrochloric acid, sulfuric acid or nitric acid may be used, although not particularly limited. The acid concentration of the acidic aqueous solution is preferably within a range of from 0.1 to 10 mol/L, more preferably within a range of from 0.1 to 3 mol/L.

The desorbing agent concentration in the desorbing agent solution is not particularly limited, and for example, it is within a range of from 1 to 99 wt %, preferably within a range of from 1 to 10 wt %.

The amount of use of the desorbing agent is not particularly limited and may, for example, be within a range of from 2 to 10,000 molar times to 1 mol of the amount of sulfur in the palladium separating agent used in the present invention, and is preferably within a range of from 5 to 1,000 molar times in view of the desorption efficiency and the economical efficiency.

By the above desorption method, a liquid containing desorbed palladium ions (hereinafter referred to as desorbed palladium ion liquid) is obtained.

The palladium ions in the desorbed palladium ion liquid may be precipitated in the form of metal palladium or a palladium complex by a known method such as reduction treatment or addition of a chelating agent, and may further by recovered by a method such as filtration.

As the method of reduction treatment of the desorbed palladium ion liquid, various methods may be employed depending upon the purpose and the equipment. For example, an electrolytic reduction method by electrolysis or a chemical reduction method of adding a reducing agent such as a boron hydride compound may be mentioned. Among them, an electrolytic reduction method by electrolysis is preferred in view of the operation efficiency and the cost.

The reduction treatment of the desorbed palladium ion liquid may be carried out under any conditions of acidic conditions, neutral conditions and basic conditions, and is preferably carried out under neutral conditions with a pH of at least 6 and at most 8, in view of the efficiency for reduction of palladium ions and with a view to suppressing corrosion of the equipment. The neutralizing agent for the desorbed palladium ion liquid is not particularly limited and is preferably an inorganic base compound such as sodium hydroxide, potassium hydroxide, sodium bicarbonate or calcium hydroxide. Among them, sodium hydroxide is more preferred as the neutralizing agent.

The reduction treatment of the desorbed palladium ion liquid is carried out usually under normal pressure in the air, but may be carried out under elevated or reduced pressure conditions or in an inert gas atmosphere. The reduction treatment is carried out usually at a temperature of from 4 to 100° C., preferably from 10 to 50° C.

As a method for filtrating precipitates of the metal palladium or the palladium complex, for example, a method of using a membrane filter, filter paper, filter cloth or a glass filter may be mentioned, and in view of operation efficiency, filtration by a membrane filter or filter paper is preferred.

The precipitates of the metal palladium or the palladium complex obtained by filtration are heated to at least the melting point of palladium and melted, whereby metal palladium with a high purity of at least 99.9% can be separated.

By the above operation, using the palladium separating agent of the present invention, separation and recovery of palladium is carried out.

The palladium separating agent of the present invention is preferably used as packed in a column or the like in view of the operation property, the transport property and the repeated use.

The column to be packed with the palladium separating agent of the present invention is preferably one made of a material excellent in the acid resistance, the base resistance and the chemical resistance, and for example, a column made of glass or an acrylic resin is preferably used. As the column, a commercially available product may be used.

The palladium separating agent of the present invention may be used in combination with an existing or commercially available adsorption and separation apparatus, and further, may be used optionally in combination with a liquid sending apparatus or the like.

EXAMPLES

Now, the present invention will be described in further detail with reference to Examples. However, it should be understood that the present invention is by no means restricted to such specific Examples.

(Analysis Method)

1. Infrared spectroscopic analysis of the palladium separating agent was carried out by a Fourier transform infrared spectrophotometer (System 2000 manufactured by PerkinElmer Japan Co., Ltd.).

2. The palladium ion concentration in an aqueous solution was measured by an ICP emission spectrometer (OPTIMA 3300DV, manufactured by PerkinElmer Japan Co., Ltd.).

3. The nitrogen content was measured by a full automatic elemental analyzer (2400II manufactured by PerkinElmer Japan Co., Ltd.).

4. The sulfur content was measured by an ion chromatography method. The ion chromatography measurement was carried out after the following pretreatment by the following apparatus under the following measurement conditions.

Pretreatment: A sample was introduced into an automatic sample combustion apparatus (AQF-100, manufactured by Mitsubishi Chemical Analytech Co., Ltd.), and $SO_4^{2-}$ formed by combustion was collected in an adsorption liquid (internal standard substance: $PO_4^-$).

Measurement apparatus: IC-2001 manufactured by Tosoh Corporation

Separation column: TSKgel Super IC-AP (4.6 mm in diameter×150 mm)

Detector: Electrical conduction detector

Eluent: 2.7 mmol/L $NaHCO_3$ and 1.8 mmol/L $Na_2CO_3$

5. The average pore size of the palladium separating agent was measured by a nitrogen adsorption method in accordance with a BET method using a measuring apparatus (model: BELSORP-mini) manufactured by BEL Japan, Inc.

6. The average particle size of the palladium separating agent was measured by a laser diffraction method using Microtrac MT3300 manufactured by NIKKISO CO., LTD.

Example 1

Preparation of Palladium Separating Agent A

Into a 50 mL eggplant flask equipped with a Dean-Stark apparatus, 2.00 g (nitrogen content: 4.28 mmol) of silica gel having its surface modified with an aminopropyl group (manufactured by KANTO CHEMICAL CO., INC., tradename: silica gel 60 (spherical) NH2), 1.03 g (8.56 mmol) of (ethylthio)acetic acid, 54 mg (0.21 mmol) of 3,5-bis(trifluoromethyl)phenylboronic acid and 20 g of xylene were weighed. Followed by reflux with heating for 18 hours. After the reaction mixture was cooled to room temperature, it was subjected to filtration, and the solid collected by filtration was washed with methanol to obtain a palladium separating agent (palladium separating agent A).

As a result of infrared spectroscopic analysis of the obtained palladium separating agent, an absorption spectrum at 1653 $cm^{-1}$ attributable to an amide bond was confirmed. The sulfur content in 1 g of the obtained palladium separating agent A was 1.6 mmol.

Example 2

Preparation of Palladium Separating Agent B

A palladium separating agent (palladium separating agent B) was obtained in the same manner as in Example 1 except that 1.29 g (8.56 mmol) of thiodiglycolic acid was used instead of 1.03 g of (ethylthio)acetic acid.

As a result of infrared spectroscopic analysis, an absorption spectrum at 1,653 cm$^{-1}$ was confirmed. The sulfur content in 1 g of the obtained palladium separating agent B was 1.4 mmol.

Example 3

Preparation of Palladium Separating Agent C

Into a 50 mL eggplant flask equipped with a Dean-Stark apparatus, 1.00 g (nitrogen content: 3.02 mmol) of silica gel having its surface modified with a 3-(ethylenediamino) propyl group (manufactured by Aldrich, tradename: 3-(ethylenediamino)propyl functional group-containing silica gel), 0.73 g (6.04 mmol) of (ethylthio)acetic acid, 39 mg (0.15 mmol) of 3,5-bis(trifluoromethyl)phenylboronic acid and 20 g of xylene were weighed, followed by reflux with heating for 18 hours. After the reaction mixture was cooled to room temperature, it was subjected to filtration, and the solid collected by filtration was washed with methanol to obtain a palladium separating agent (palladium separating agent C).

As a result of infrared spectroscopic analysis, an absorption spectrum at 1,653 cm$^{-1}$ was confirmed. The sulfur content in 1 g of the obtained palladium separating agent C was 1.3 mmol.

Example 4

0.2 g of the palladium separating agent A was dispersed in water, and the dispersion was packed in a glass column (inner diameter: 5 mm, length: 100 mm). 50 mL of a 1 mol/L hydrochloric acid aqueous solution containing 400 mg/L of each of palladium ions and platinum ions was passed through the column from the column top at a flow rate of 36 mL/Hr, whereby the metal ions were adsorbed. Then, 20 mL of water was passed through the column (at a flow rate of 36 mL/Hr) to wash the column, and then 50 mL of a 1 mol/L hydrochloric acid aqueous solution containing thiourea at a concentration of 5 wt % was passed through the column from the column top at a flow rate of 36 mL/Hr, whereby the metal ions adsorbed in the palladium separating agent A were desorbed. In the obtained column effluent (hereinafter referred to as recovered liquid), the palladium ion concentration was 395 mg/L and the platinum ion concentration was 6 mg/L, and the palladium ions were highly selectively separated and recovered. Further, the palladium ion adsorption amount was calculated from the palladium ion concentration in the recovered liquid, whereupon it was 98.7 mg per 1 g of the palladium separating agent A.

Example 5

Palladium ions were separated and recovered in the same manner as in Example 4 except that 0.2 g of the palladium separating agent B was used instead of 0.2 g of the palladium separating agent A. As a result, in the recovered liquid, the palladium ion concentration was 356 mg/L and the platinum ion concentration was 2 mg/L, and the palladium ions were highly selectively separated and recovered. Further, the palladium ion adsorption amount was calculated from the palladium ion concentration in the recovered liquid, whereupon it was 88.9 mg per 1 g of the palladium separating agent B.

Example 6

Palladium ions were separated and recovered in the same manner as in Example 4 except that 0.2 g of the palladium separating agent C was used instead of 0.2 g of the palladium separating agent A. As a result, in the recovered liquid, the palladium ion concentration was 314 mg/L and the platinum ion concentration was 18 mg/L, and the palladium ions were highly selectively separated and recovered. Further, the palladium ion adsorption amount was calculated from the palladium ion concentration in the recovered liquid, whereupon it was 78.5 mg per 1 g of the palladium separating agent C.

Example 7

0.1 g of the palladium separating agent A was dispersed in water, and the dispersion was packed in a glass column (inner diameter: 5 mm, length: 100 mm). 50 mL of a 1 mol/L hydrochloric acid aqueous solution (hereinafter referred to as a test solution) containing various metal ions at concentrations as shown in Table 1, prepared by using metal standard solutions and a hydrochloric acid aqueous solution, was passed through the column from the column top at a flow rate of 36 mL/Hr, whereby the metal ions were adsorbed. Then, 20 mL of water was passed through the column (at a flow rate of 36 mL/Hr) to wash the column, and then 50 mL of a 1 mol/L hydrochloric acid aqueous solution containing thiourea at a concentration of 5 wt % was passed through the column from the column top at a flow rate of 36 mL/Hr, whereby the metal ions were desorbed. The results of measurement of the metal ion concentrations in the obtained recovered liquid are shown in Table 1. By the above operation, palladium ions were highly selectively separated and recovered. Further, the palladium ion adsorption amount was calculated from the palladium ion concentration in the recovered liquid, whereupon it was 94.5 mg per 1 g of the palladium separating agent A.

TABLE 1

| Metal contained | Pd | Pt | Rh | Cu | Fe | Ni | Zn |
| --- | --- | --- | --- | --- | --- | --- | --- |
| Metal concentration in test solution (mg/L) | 198 | 607 | 21 | 20 | 21 | 20 | 20 |
| Metal concentration in recovered liquid (mg/L) | 189 | 5 | * | * | * | * | * |

* Detection limit or lower

Example 8

0.1 g of the palladium separating agent A was dispersed in water, and the dispersion was packed in a glass column (inner diameter: 5 mm, length: 100 mm). 50 mL of a 1 mol/L hydrochloric acid aqueous solution containing 200 mg/L of each of palladium ions and platinum ions was passed through the column from the column top at a flow rate of 36 mL/Hr, whereby the metal ions were adsorbed. Then, 20 mL of water was passed through the column (at a flow rate of 36 mL/Hr) to wash the column, and then 50 mL of a 1 mol/L hydrochloric acid aqueous solution containing thiourea at a concentration of 5 wt % was passed through the column from the column top at a flow rate of 36 mL/Hr, whereby the metal ions were desorbed. The palladium ion adsorption amount was calculated from the palladium ion concentration in the recovered liquid. Then, 20 mL of water was passed through the column (at a flow rate of 36 mL/Hr to wash the column. Separation and recovery of palladium ions was carried out continuously 5 cycles, one cycle comprising the above operation to separate and recover the palladium ions, to evaluate the durability of the palladium separating agent A. As a result, as shown in Table 2, the palladium ions were highly selectively separated and recovered at every cycle. Further, in the continuous cycles, the palladium ion adsorption amount was not decreased, and the palladium separating agent A could be repeatedly used.

TABLE 2

|  | Number of repetition | | | | |
| --- | --- | --- | --- | --- | --- |
|  | 1 | 2 | 3 | 4 | 5 |
| Palladium ion concentration in recovered liquid (mg/L) | 196 | 197 | 197 | 198 | 196 |
| Platinum ion concentration in recovered liquid (mg/L) | 3 | 3 | 3 | 3 | 2 |
| Palladium adsorption amount (mg/g) | 98.0 | 98.8 | 98.4 | 98.8 | 98.0 |

Example 9

Separation and recovery of palladium ions was carried out in the same manner as in Example 4 except that the hydrochloric acid concentration of the test solution at the time of adsorption operation was 5 mol/L. As a result, in the recovered liquid, the palladium ion concentration was 396 mg/L and the platinum ion concentration was 3 mg/L, and palladium ions were highly selectively separated and recovered. Further, the palladium ion adsorption amount was calculated from the palladium ion concentration in the recovered liquid, whereupon it was 99.0 mg per 1 g of the palladium separating agent A.

Example 10

(1) Preparation of Palladium Separating Agents Used in Examples 11 to 20

A palladium separating agent of the formula (6) schematically illustrated including bonding of the functional group to the carrier, was prepared in accordance with the following method. Further, in the same manner, palladium separating agents having various S/N (element ratios) were prepared.

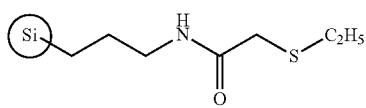

(6)

Into a 500 mL eggplant flask equipped with a Dean-Stark apparatus, 100 g of each silica gel (manufactured by FUJI SILYSIA CHEMICAL LTD., tradename: PSQ60B, PSQ100B, PSQ60AB, MB4B30-50 or MB4B30-200), 5 g of water and 200 g of o(ortho)-xylene were weighed, and while they were vigorously stirred at 60° C., a preliminarily prepared mixed solution of 35.9 g of 3-aminopropyltrimethoxysilane and 35.9 g of o-xylene was dropwise added thereto over a period of 10 minutes, and then the mixture was heated to 90° C. and stirred for one hour. Then, the mixture was heated to 110° C. and stirred for 1.5 hours. A mixed solution of methanol, o-xylene and water accumulated in the Dean-Stark apparatus was discharged out of the system.

Then, 0.005 g of 3,5-bis(trifluoromethyl)phenylboronic acid and a predetermined amount of (ethylthio)acetic acid were weighed, followed by reflux with heating for from 2 to 24 hours with vigorous stirring. After the reaction mixture was cooled to room temperature, it was subjected to filtration, and the solid collected by filtration was washed with methanol to obtain a palladium separating agent.

(2) Preparation of Palladium Separating Agents Used in Examples 21 to 27

A palladium separating agent of the formula (7) schematically illustrated including the bonding of the functional group to the carrier, was prepared in accordance with the following method. Further, in the same manner, palladium separating agents having various substituents were prepared.

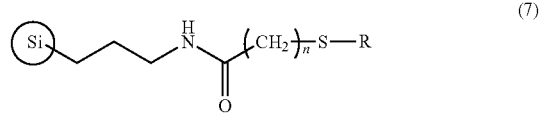

(7)

Palladium separating agents were obtained in the same manner as in Examples 11 to 20 except that various corresponding carboxylic acids were used instead of (ethylthio) acetic acid used in Examples 11 to 20.

Examples 11 to 27

As the palladium separation performance of each of the palladium separating agents obtained in (1) and (2) in Example 10, the saturated adsorption amount and the selective adsorption ratio of palladium ions were evaluated.

Adsorption liquids A and B used to evaluate the separation performance are as follows.

Adsorption liquid A: A 1M hydrochloric acid solution containing 200 mg/L of palladium(II) ions and 200 mg/L of platinum(IV) ions.

Adsorption liquid B: A 1M hydrochloric acid solution containing 6,000 mg/L of palladium(II) ions and 30,000 mg/L of platinum(IV) ions.

Further, the palladium selectivity was calculated in accordance with the following formula:

Pd selectivity (%)=(palladium ion amount in the column effluent)/{(palladium ion amount in the column effluent)+(platinum ion amount in the column effluent)}×100%

(1) Palladium Ion Saturated Adsorption Amount 0.22 g of each palladium separating agent was accurately weighed in a 30 mL glass container, and 20 mL of a 1,000 mg/L palladium standard solution (manufactured by Wako Pure Chemical Industries Ltd.) was added, followed by stirring for 2 hours. The palladium ion concentration in the obtained solution was measured, and the palladium ion saturated adsorption amount of each palladium separating agent was calculated.

(2) Selective Adsorption Ratio of Palladium Ions 0.2 g of each palladium separating agent was dispersed in water, and the dispersion was packed in a glass column (inner diameter: 5 mm, length: 100 mm). The adsorption liquid A or B containing palladium ions and platinum ions at predetermined concentrations was passed through the column from the column top at a flow rate of 36 mL/hour, whereby the metal ions were adsorbed, and at the time when the composition of the liquid at the outlet of the column became the same as the composition of the original adsorption liquid, passing of the adsorption liquid was terminated. Then, 20 mL of water was passed through the column at a flow rate of 36 mL/Hr to wash the column, and then 50 mL of a 1 mol/L hydrochloric acid aqueous solution containing thiourea at a concentration of 5 wt % was passed through the column from the column top at a flow rate of 36 mL/Hr, whereby the metal ions adsorbed in each palladium separating agent were desorbed. From the palladium ion concentration and the platinum ion concentration in the obtained column effluent, the selective adsorption ratio of palladium ions in each palladium separating agent was calculated.

In Tables 3 and 4, physical properties such as the sulfur content, and results of evaluation of the palladium separation performance, of the respective palladium separating agents obtained in (1) and (2) in Example 10 are shown.

in the case of the adsorption liquid A having low palladium ion and platinum ion concentrations, the palladium selectivity was less than 93% in the case of the adsorption liquid B having high palladium ion and platinum ion concentrations, and the selectivety was slightly lowered as compared with Examples 1 to 17.

INDUSTRIAL APPLICABILITY

The palladium separating agent of the present invention is capable of separating palladium ions from a solution containing palladium ions in a short time with a high selectivity, can be repeatedly used, and is widely used in the field of

TABLE 3

| | Ex. 11 | Ex. 12 | Ex. 13 | Ex. 14 | Ex. 15 | Ex. 16 | Ex. 17 | Ex. 18 | Ex. 19 | Ex. 20 |
|---|---|---|---|---|---|---|---|---|---|---|
| Physical properties of separating agent | | | | | | | | | | |
| Pore size (nm) | 4 | 4 | 4 | 4 | 4 | 4 | 2.5 | 4 | 4 | <1 |
| Sulfur content (mmol/g) | 1.43 | 1.43 | 1.40 | 1.34 | 1.40 | 1.31 | 1.34 | 1.31 | 1.15 | 0.79 |
| Nitrogen content (mmol/g) | 1.43 | 1.43 | 1.43 | 1.43 | 1.43 | 1.36 | 1.43 | 1.43 | 1.50 | 0.79 |
| S/N (element ratio) | 1.00 | 1.00 | 0.98 | 0.94 | 0.98 | 0.96 | 0.94 | 0.92 | 0.77 | 1.00 |
| Average particle size (μm) | 40 | 60 | 60 | 60 | 100 | 250 | 60 | 60 | 60 | 110 |
| Result of evaluation of Pd separation performance | | | | | | | | | | |
| PD saturated adsorption amount (g/g agent) | 0.081 | 0.081 | 0.081 | 0.081 | 0.074 | 0.071 | 0.073 | 0.080 | 0.075 | 0.005 |
| Pd selectivity (%) in the case of adsorption liquid A | 99.8 | 99.8 | 99.7 | 99.4 | 99.5 | 99.6 | 99.4 | 99.0 | 98.8 | 97.2 |
| Pd selectivity (%) in the case of adsorption liquid B | 98.5 | 98.5 | 97.3 | 95.5 | 97.3 | 95.0 | 95.5 | 92.3 | 92.0 | — |

TABLE 4

| | Ex. 21 | Ex. 22 | Ex. 23 | Ex. 24 | Ex. 25 | Ex. 26 | Ex. 27 |
|---|---|---|---|---|---|---|---|
| Physical properties of separating agent | | | | | | | |
| Pore size (nm) | 4 | 4 | 4 | 4 | 4 | 4 | 4 |
| R | Ethyl | Ethyl | Methyl | Isopropyl | Phenyl | Benzyl | 2-pyridyl |
| Number of n | 3 | 4 | 1 | 1 | 1 | 1 | 1 |
| Sulfur content (mmol/g) | 1.13 | 1.13 | 1.34 | 1.32 | 1.29 | 1.19 | 1.03 |
| Nitrogen content (mmol/g) | 1.43 | 1.43 | 1.43 | 1.43 | 1.37 | 1.37 | 2.43 |
| S/N (element ratio) | 0.79 | 0.79 | 0.94 | 0.92 | 0.94 | 0.88 | 0.42 |
| Average particle size (μm) | 60 | 60 | 60 | 60 | 60 | 60 | 60 |
| Result of evaluation of Pd separation performance | | | | | | | |
| Pd saturated adsorption amount (g/g agent) | 0.065 | 0.065 | 0.082 | 0.074 | 0.067 | 0.065 | 0.090 |
| Pd selectivity (%) in the case of adsorption liquid A | 98.1 | 97.5 | 99.1 | 99.5 | 99.9 | 99.4 | 83.3 |

As evident from Table 3, in Examples 11 to 17, the palladium seperating agents had a S/N (element ratio) of at at least 0.94 and an average pore size of the carrier of at least 2 nm, the palladium selectively was at least 99.4% in the case of the adsorption liquid A having low palladium ion and platinum ion concentrations, and even in the case of the adsorption liquid B having high palladium ion and platinum ion concentrations, the palladium selectively was at least 95%, and high selectivity was obtained.

Whereas in Examples 18 to 20, the palladium seperating agents had a S/N (element ratio) less than 0.94 or an average pore size of the carrier less than 1 nm, and although modestly favorable palladium ion selectivety was obtained recovering precious metals in view of economical efficiency and the environmental preservation.

The entire disclosure of Japanese Patent Application No. 2011-223423 filed on Oct. 7, 2011 including specification, claims, drawings and summary is incorporated herein by reference in its entirety.

The invention claimed is:

1. A palladium separating agent which selectively adsorbs palladium ions and which comprises a functional group represented by the formula (2) bonded to an inorganic carrier by means of a methylene group pre-bonded to the inorganic carrier, an ethylene group pre-bonded to the inorganic carrier, a $C_{3-8}$ linear alkylene group pre-bonded to the inorganic carrier, or a $C_{3-8}$ branched alkylene group pre-bonded to the inorganic carrier:

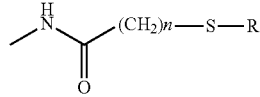 (2)

wherein R is a $C_{1-18}$ chain hydrocarbon group, a $C_{3-10}$ alicyclic hydrocarbon group, a $C_{6-14}$ aromatic hydrocarbon group, a carboxymethyl group or a carboxyethyl group, and n is an integer of from 1-4.

2. The palladium separating agent according to claim 1, wherein the functional group represented by the formula (1) is bonded to the inorganic carrier by means of a n-propylene group pre-bonded to the inorganic carrier.

3. The palladium separating agent according to claim 1, wherein R in the formula (2) is a methyl group, an ethyl group, a propyl group, a butyl group, an isopropyl group, a phenyl group or a benzyl group.

4. The palladium separating agent according to claim 1, wherein the inorganic carrier is a silica gel.

5. A method for producing the palladium separating agent according to claim 1, which comprises reacting a sulfide-containing carboxylic acid compound represented by the formula (3) with an inorganic carrier having an amino group to obtain the palladium separating agent which comprises a function group represented by the formula (2) bonded to the inorganic carrier by means of a methylene group pre-bonded to the inorganic carrier, an ethylene group pre-bonded to the inorganic carrier, a $C_{3-8}$ linear alkylene group pre-bonded to the inorganic carrier, or a $C_{3-8}$ branched alkylene group pre-bonded to the inorganic carrier:

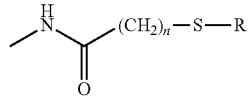 (2)

wherein R is a $C_{1-16}$ chain hydrocarbon group, a $C_{3-10}$ alicyclic hydrocarbon group, a $C_{6-14}$ aromatic hydrocarbon group, a carboxymethyl group or a carboxyethyl group, n is an integer of from 1 to 4;

 (3)

wherein R is a $C_{1-16}$ chain hydrocarbon group, a $C_{3-10}$ alicyclic hydrocarbon group, a $C_{6-14}$ aromatic hydrocarbon group, a carboxymethyl group, a carboxyethyl group, and n is an integer of from 1 to 4.

6. The method for producing the palladium separating agent according to claim 5, wherein the inorganic carrier having an amino group is one obtained by reacting a silane coupling agent having an amino group represented by the formula (4) with an inorganic carrier

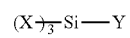 (4)

wherein each of X's which are independent of one another, is a methyl group, an ethyl group, a methoxy group or an ethoxy group, provided that at least one of them is a methoxy group or an ethoxy group, and Y is a $C_{1-12}$ aminoalkyl group having from 1 to 2 nitrogen atoms.

7. A method for adsorbing palladium ions, which comprises bringing a palladium separating agent as defined in claim 1 into contacted with a solution containing palladium ions.

8. A method for desorbing palladium ions, which comprises bringing the palladium separating agent in which palladium ions are adsorbed, obtained by the method for adsorbing palladium ions as defined in claim 7, into contact with a desorbing agent.

9. The method for desorbing palladium ions according to claim 8, wherein the desorbing agent is ammonia, thiourea or methionine.

10. A chromatography column, comprising the palladium seperating agent as defined in claim 1.

* * * * *